(12) United States Patent
Sjoblom et al.

(10) Patent No.: US 10,145,820 B2
(45) Date of Patent: Dec. 4, 2018

(54) IDENTIFICATION OF WATER PIPE MATERIAL BASED ON STRESS WAVE PROPAGATION

(71) Applicant: Drexel University, Philadelphia, PA (US)

(72) Inventors: Kurt Sjoblom, Boxborough, MA (US); Matteo Mazzotti, Philadelphia, PA (US); Charles Nathan Haas, Philadelphia, PA (US); Ivan Bartoli, Ardmore, PA (US)

(73) Assignee: Drexel University, Philadelphia, PA (US)

( * ) Notice: Subject to any disclaimer, the term of this patent is extended or adjusted under 35 U.S.C. 154(b) by 148 days.

(21) Appl. No.: 15/447,165

(22) Filed: Mar. 2, 2017

(65) Prior Publication Data

US 2017/0254782 A1 Sep. 7, 2017

Related U.S. Application Data

(60) Provisional application No. 62/302,701, filed on Mar. 2, 2016.

(51) Int. Cl.
*G01N 29/04* (2006.01)
*G01N 29/24* (2006.01)
*G01N 29/44* (2006.01)
*G01N 29/07* (2006.01)
*G01V 1/00* (2006.01)

(52) U.S. Cl.
CPC ........... *G01N 29/07* (2013.01); *G01N 29/045* (2013.01); *G01N 29/2475* (2013.01); *G01N 29/4427* (2013.01); *G01V 1/00* (2013.01)

(58) Field of Classification Search
CPC .. G01N 29/045; G01N 29/2475; G01N 29/07; G01N 29/4427; G01V 1/00
USPC ............................................................ 73/597
See application file for complete search history.

(56) References Cited

U.S. PATENT DOCUMENTS

| 4,455,863 | A | * | 6/1984 | Huebler | ................ | G01M 3/243 |
| | | | | | | 73/40.5 A |
| 5,675,506 | A | * | 10/1997 | Savic | ........................ | F17D 5/06 |
| | | | | | | 702/51 |
| 6,202,490 | B1 | * | 3/2001 | Taniguchi | .............. | G01B 17/00 |
| | | | | | | 73/579 |
| 6,275,705 | B1 | * | 8/2001 | Drane | ..................... | G01S 1/024 |
| | | | | | | 342/357.31 |
| 6,530,263 | B1 | * | 3/2003 | Chana | ....................... | F17D 5/06 |
| | | | | | | 73/40.5 A |

(Continued)

*Primary Examiner* — J M Saint Surin
(74) *Attorney, Agent, or Firm* — Schott, P.C.

(57) ABSTRACT

A nondestructive evaluation method for determining the material used in a below ground service line includes inserting a probe with a wave measurement device therein into an area corresponding to a location of a service line; inciting a service line wave through an exposed portion of the service using a vibratory shaker; measuring, by the wave measurement device, a substrate wave created by the service line wave passing thought the service line and into the substrate; identifying, by a data acquisition system, the service line wave velocity; comparing the service line wave velocity to a known set of wave velocities in service line according to a service line material; and identifying the service line material in the service line by comparing the wave velocity in the service line with the known set of wave velocities.

20 Claims, 2 Drawing Sheets

(56) References Cited

U.S. PATENT DOCUMENTS

2016/0011152 A1\* 1/2016 Georgeson ........... G01N 29/043
                                                                               73/655

\* cited by examiner

IDENTIFICATION OF WATER PIPE MATERIAL BASED ON STRESS WAVE PROPAGATION

BACKGROUND

In 1991, the US EPA published the 'Lead and Copper Rule' (LCR) regulation to address the widespread legacy use of lead pipes for potable water delivery and service lines. While well-intended, the regulation received immediate push-back from municipal water utility companies that cited compliance with the regulation was too difficult to implement in the LCR's time-line and owner-utility responsibility was ill-defined. As a result, the American Water Works Association (AWWA) sued the EPA in 1993 and a Federal Appeals Court partially sided with the AWWA. After several years of back and forth, the LCR was amended in 2000 to allow for utility companies to perform partial replacements of water delivery lines. This made the problem worse, as it allowed for the utility companies to replace main water lines, but leave the lead service lines intact and the responsibility of the landowner to complete the replacement. This has left many homeowners unsure or falsely sure of whether their service lines are made of lead.

This issue has come to the forefront of the Nation's attention due to the recent problems found in Flint, Mich. Flint is not alone in their plight in dealing with this issue, nearly all urban areas have used and continue to have lead service and distribution lines. This problem is particularly worse in older and larger cities including Washington, D.C., Boston and Philadelphia due to scarce records of the original pipe installations.

Considering this history, there is a current need to rapidly and cost effectively identify the service line material supplying water to homeowners and residents in urban areas. Since visual line inspection or water sampling are the current methods for line material testing—the former is time and effort consuming, and the latter is costly and unreliable.

SUMMARY OF THE INVENTION

A nondestructive evaluation method for determining the material used in a below ground service line includes inserting a probe with a wave measurement device therein into an area corresponding to a location of a service line; generating a service line wave through an exposed portion of the service using a vibratory shaker; measuring, by the wave measurement device, a substrate wave created by the service line wave passing thought the service line and into the substrate; identifying, by a data acquisition system, the service line wave velocity; comparing the service line wave velocity to a known set of wave velocities in service line according to a service line material; and identifying the service line material in the service line by comparing the wave velocity in the service line with the known set of wave velocities.

Figure 1:
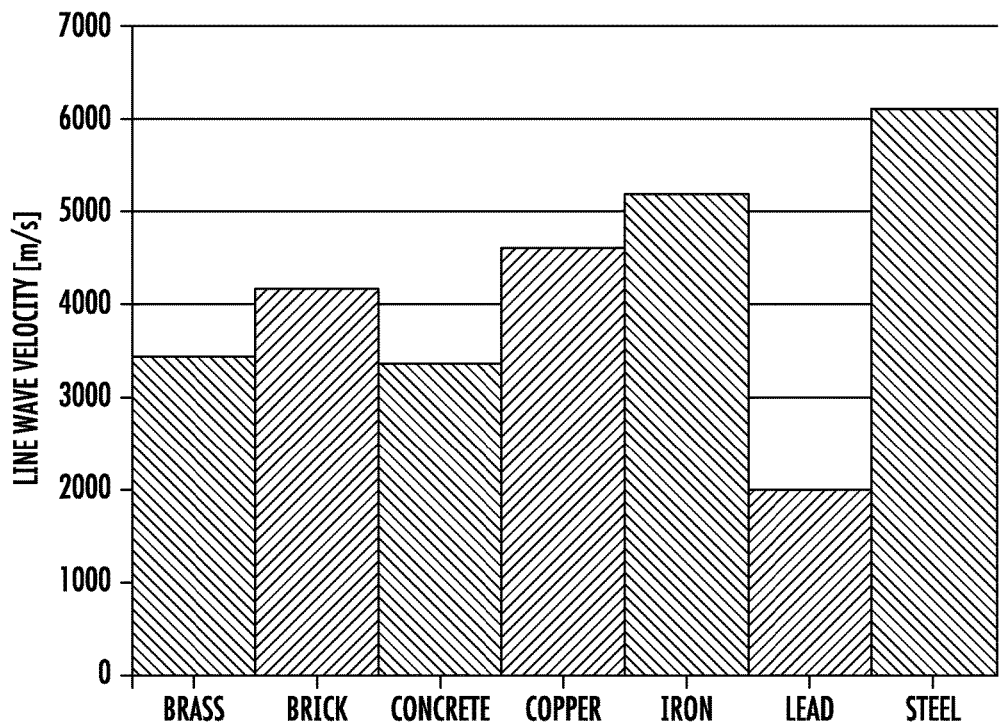
FIG. 1 shows a graph of sound wave velocities in various materials.

DETAILED DESCRIPTION OF THE EMBODIMENTS 1.0 Review of NDE Techniques for the Detection and Location of Pipelines Common nondestructive evaluation (NDE) methods have different advantages and limitations when applied to the detection, location and material characterization of buried pipelines. Some of these methods are briefly reviewed in the following.

1.1 Closed Circuit Television (CCTV)

Originally introduced in the 1960s for the detection of leaks in pipes and sewers, this system used of a television camera inserted in the pipe and remotely controlled by an operator. Visual observation includes the collection and inspection of CCTV images for material recognition, which is usually a slow process. Moreover, these methods may require a pipe to be drained before inspection, resulting in high operative costs.

1.2 Electromagnetic Induction (EMI) Methods

Current state-of-the-art electromagnetic induction (EMI) metal detectors can detect small metal objects at shallow depths and large metal objects at greater depths under a wide range of environmental and soil conditions. The method introduces an electromotive force in the pipe, which in turn causes eddy currents to flow in the metal. The method compares the measured decay in time of such currents, which depends on the size, shape, and magnetic properties (conductivity and permeability) of the metal, to a signature library of conductive objects, thus enabling the detection and classification of the pipe.

A method based on eddy currents, the Remote Field Eddy Current (RFEC) method, has been also developed for the inspection of both ferromagnetic and non-ferromagnetic conducting tubular from the inside.

Based upon this method, a hydroscope may enable nondestructive evaluation of buried cast or ductile iron and steel pipes. This technique assesses the condition of water pipelines by sensing the changes in an electromagnetic signal as it passes through the pipe wall, which helps characterize the material.

1.3 Ground Penetrating Radar (GPR)

Ground Penetrating Radar (GPR) constitutes a well-established technology that uses electromagnetic waves to identify buried objects by detecting their reflections. Whenever a radar pulse strikes a boundary interface of contrasting dielectrics, a portion of the radar wave reflects back to the surface and a receiving antenna records it. The typical feature used to locate the pipes are hyperbolic patterns of the time of flight generated by a linear scan of the antenna above the surface (reflected signal traces).

Although different algorithms that use GPR data have been successfully developed for detection and geometric characterization purposes (including the effect of fluid interface), the material characterization of the buried pipe remains a challenging task. Moreover, the depth of penetration is greatly reduced in presence of conductive soils such as clay and saturated soils, which induce high signal attenuation.

1.4 Broadband Electromagnetics/Wave Impedance Probe (WIP)

The broadband EM technique is a hybrid of Ground Penetrating Radar and electromagnetic techniques, able to detect differences in the electromagnetic impedance of the tested material. Although the system is suited for pipelines of relatively small diameter (>200 mm) and shallow surveys at the 0.5-10.0 m scale, it may not be useful for other pipelines as well.

1.5 Infrared Thermography (IR)

This method relies on the use of an infrared scanner, sensitive to short- or medium-wave infrared radiation, to measure variations in temperature produced by the effect of the pipeline, which it converts into thermographic images in which objects are represented by their thermal rather than their optical values. However, as with the GPR, the location using infrared thermography is affected by the properties of the surrounding ground, and in particular moisture content. Similarly, ground cover and wind speed may influence results. The greatest drawback however is its inability to measure depth.

2.0 Alternate Method of Detecting Pipe Material

While these methods provide some vision of buried infrastructure, most face challenges in quickly and accurately characterizing the service line material. A non-destructive evaluation may measure the velocity of a propagating stress wave through a length of line. Because stress waves travel at significantly different velocities within various materials as illustrated by FIG. 1, a measurement of the velocity of a stress wave will give an indication to the presence of lead. This may be seen in FIG. 1 that shows a set of service line wave velocities according to material where the wave speed in lead is ½ to ⅓ to that in other common pipe materials.

Figure 2:
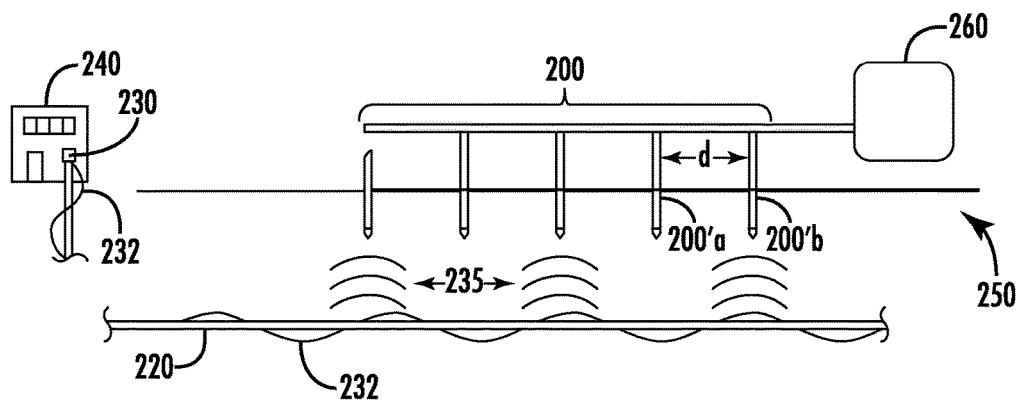
FIG. 2 shows a schematic of the proposed method.

FIG. 2 shows an implementation of a nondestructive evaluation apparatus that may use this wave measurement technology. As shown, a vibratory shaker 230 attached to an accessible/exposed service line 220 located within or outside a building 240, generates a vibration and service line wave 232 in the service line 220. The service line wave 232 propagates along the service line 220 and into the substrate as substrate waves 235. Accelerometers within accelerometer probes 200 detect the substrate waves 235 and transmit data regarding the substrate waves 235 to a data acquisition unit DAQ 260 that analyzes the data and issues projections about the service line 220 material.

The below subsections give more detail about each of these components and their application.

2.1 Accelerometers

The accelerometer probes 200 first would be inserted into the ground/substrate 250. The accelerometer probes 200 may be placed in a line, grid, or other pattern corresponding to an area where a user believes a service line 220 to be. A grid pattern helps attain reliable readings of a wave 235 traveling through the substrate 250 because a grid patterns gives more readings, which minimize the effects of voids and varying substrate 250 conditions. A minimum of 2 accelerometer probes 200 in theory and 4 accelerometer probes in practice give baseline acceptable results. And even more give even better results.

Within the grid, line, or other pattern, the distance between accelerometer probes 200 may ideally be between 15 cm to 5 m to a depth from the surface to just below the pavement and/or backfill line. The closer the accelerator probe 200 tip gets to the line 220, the more accurate the data received.

Figure 3:
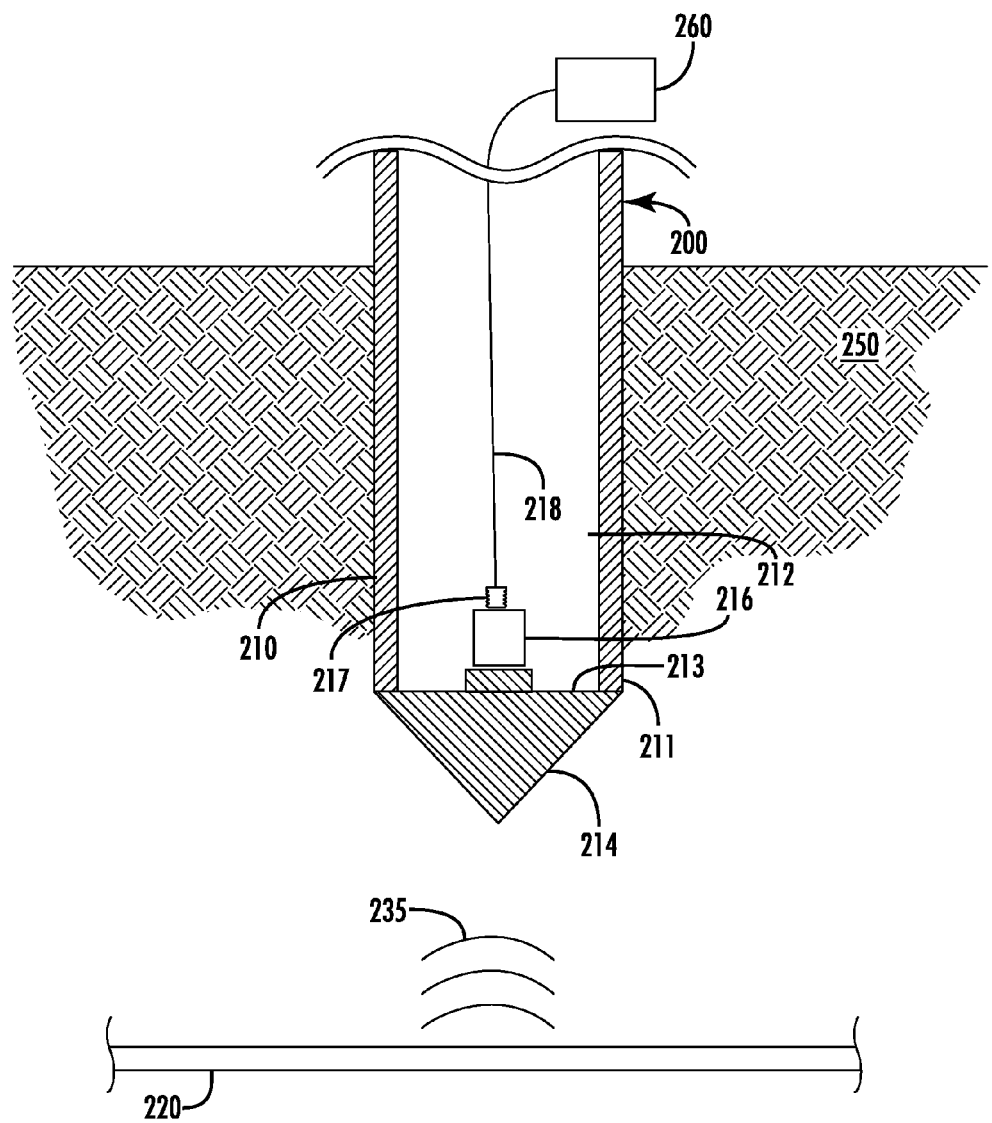
FIG. 3 shows a detailed view of an accelerometer probe.

FIG. 3 shows a detailed view of an accelerometer probe 200. The probe 200 includes a protective sheath 210 that is inserted or follows a drilled hole into the substrate 250. The sheath 210 includes a hollow portion with a cavity 212 and protective or hardened tip 214. The tip 214 may be made from stainless steel or other corrosion resistant and hardened material and may be integral with, or detachable from, a main body 211 of the sheath 210.

The sheath 210 may be 0.5 inches wide and as long as necessary to place the sheath tip 214 in close proximity to the service line 220. Within the hollow portion 212 and resting on a platform 213 provided by the tip 214 is the accelerometer 216. The accelerometer 216 may include an electrical connector 217 engaged to an electrical wire 218 that transmits data to the DAQ 260. Although a wire 218 is shown, the accelerometer 216 may communicate with the DAQ 260 wirelessly.

The accelerometer 216 may rest on a protective mounting 215 to minimize the effect of any damaging impacts to the tip 214.

Although this application describes accelerometers 216, other wave/vibration measurement devices may also be used such as geophone sensors, impact echo sensors, or acoustic emission sensors.

2.2 Excitation

Once the accelerometer probes 200 are in place, a user begins to send various service line waves 232 through the line 220 via a hammer (not shown) or the vibratory shaker 230. This shaker 230 imparts a frequency varying excitation to the water line 220 in the building 240 that propagates out through the service line 220. In use, a user may send a broad range of amplitudes and frequencies through the line 220 from 0.01 kHz to 1,000 kHz. The lower frequency waves will not react to corrosion and other defects in the line 220 in the same way that higher frequency waves will, but the variety of waves traveling through the line 220 will give the DAQ 260 more data points.

As the waves 235 travel through the service line 220, some of the energy of the wave may be lost to the substrate 250. This loss may travel to the embedded probes 200 and be identified via the DAQ 260.

2.3 Measurement and Data Acquisition

Referring again to FIG. 2, as the service line wave 232 travels through the line 220, it excites substrate waves 235 that are detected by the accelerometer probes 200. To measure the velocity that the service line wave 232 is traveling through the line 220, the DAQ 260 may record the distance "d" between a first and second probe 200a, 200b and the time elapsed between receipt of the substrate wave 235 detection at each probe 200a, 200b. The velocity of the shaker wave 232 may be measured by dividing the distance d by this time.

The DAQ 260 or other processor may then compare this velocity to known velocities in various material service lines 220 to determine the material used in the line 220, as shown in FIG. 1, for example.

In use, the DAQ 260 collects many data points from the various waves and frequencies and performs statistical analysis to discard outlier data that may be caused by tree roots, pipe irregularities, substrate changes, etc. to arrive at a projected line wave speed and material.

The above method and apparatus may yield rapid testing times of approximately 1 hour and result in minimal disturbance to the pavement/sidewalk/ground.

While the invention has been described with reference to the embodiments above, a person of ordinary skill in the art would understand that various changes or modifications may be made thereto without departing from the scope of the claims.

The invention claimed is:

1. A nondestructive evaluation method for determining a material used in a below ground service line comprising:
    inserting a probe with a wave measurement device therein into an area corresponding to a location of a service line;
    generating a service line wave through an exposed portion of the service line using a vibratory shaker;
    detecting, by the wave measurement device, at least two substrate waves created by the service line wave passing through the service line and into a substrate;
    identifying, by a data acquisition system, a velocity of the service line wave using the detected at least two substrate waves;
    comparing the velocity of the service line wave to a known set of wave velocities corresponding to different service line materials; and
    identifying a service line material in the service line by comparing the velocity of the service line wave with the known set of wave velocities corresponding to different service line materials.

2. The nondestructive evaluation method of claim 1, wherein the detecting is done using more than one probe.

3. The nondestructive evaluation method of claim 2, wherein at least two probes are spaced at a distance from one another.

4. The nondestructive evaluation method of claim 3, wherein a first probe and a second probe of the probes detect the substrate wave at different times.

5. The nondestructive evaluation method of claim 4, further comprising calculating the velocity of the service line wave by dividing the distance by a differences in the different times.

6. The nondestructive evaluation method of claim 2, wherein the wave measurement devices comprise accelerometers.

7. The nondestructive evaluation method of claim 6, wherein the accelerometers are located within a protective sheath.

8. The nondestructive evaluation method of claim 1, wherein the generation of a service line wave is done using a vibratory shaker attached to the service line.

9. The nondestructive evaluation method of claim 1, wherein the service line wave has a frequency of between 0.01 kHz to 1,000 kHz.

10. The nondestructive evaluation method of claim 1, wherein an amplitude of the service line is adjusted.

11. A nondestructive evaluation apparatus for determining a material used in a below ground service line comprising:
    a probe with a wave measurement device therein, wherein each probe is configured for insertion into an area corresponding to a location of a service line;
    a vibratory shaker that generates a service line wave through an exposed portion of the service line;
    a wave measurement device that detects at least two substrate waves created by the service line wave passing through the service line and into a substrate;
    a data acquisition system that identifies a velocity of the service line wave using the detected at least two substrate waves; and
    a processor that compares the velocity of the service line wave to a known set of wave velocities corresponding to different service line materials and identifies a service line material in the service line by comparing the velocity of the service line wave with the known set of wave velocities corresponding to different service line materials.

12. The nondestructive evaluation apparatus of claim 11, further comprising more than one probe.

13. The nondestructive evaluation apparatus of claim 12, wherein at least two probes are spaced at a distance from one another.

14. The nondestructive evaluation apparatus of claim 13, wherein a first probe and a second probe of the probes detect the substrate wave at different times.

15. The nondestructive evaluation apparatus of claim 14, further comprising calculating the velocity of the service line wave by dividing the distance by a differences in the different times.

16. The nondestructive evaluation apparatus of claim 11, wherein the wave measurement device is an accelerometer.

17. The nondestructive evaluation apparatus of claim 16, wherein the probe comprises a cavity in which the accelerometer is located.

18. The nondestructive evaluation apparatus of claim 11, wherein the probe comprises a hardened tip.

19. The nondestructive evaluation apparatus of claim 11, wherein the service line wave has a frequency of between 0.01 kHz to 1,000 kHz.

20. The nondestructive evaluation apparatus of claim 11, wherein the vibratory shaker adjusts an amplitude of the service line wave.

* * * * *